United States Patent [19]

Dragan et al.

[11] Patent Number: 5,172,807
[45] Date of Patent: Dec. 22, 1992

[54] CEMENT MIXING CAPSULE

[75] Inventors: William B. Dragan, Easton; John Discko, Jr., Hamden, both of Conn.

[73] Assignee: Centrix, Inc., Shelton, Conn.

[21] Appl. No.: 767,623

[22] Filed: Sep. 30, 1991

[51] Int. Cl.⁵ .............................................. B65D 25/08
[52] U.S. Cl. ..................................... 206/219; 206/221; 206/222; 206/63.5; 222/82; 222/136; 222/91; 222/145; 433/90; 604/87
[58] Field of Search ............... 206/63.5, 219, 221, 206/222, 384; 215/DIG. 8; 604/87, 200; 222/80, 82, 91, 136, 145, 327, 386, 572, 574; 433/90

[56] References Cited

U.S. PATENT DOCUMENTS

| Re. 33,801 | 1/1992 | Green | 222/82 |
|---|---|---|---|
| 622,222 | 4/1899 | Greene | 222/574 |
| 2,106,577 | 1/1938 | Sherbondy | 206/384 |
| 2,773,591 | 12/1956 | Jensen | 206/221 |
| 3,028,052 | 4/1962 | Archer | 222/136 |
| 3,245,598 | 2/1966 | Kobernick | 206/222 |
| 3,291,128 | 12/1966 | O'Neil | 222/386 |
| 3,370,754 | 2/1968 | Cook et al. | 222/136 |
| 3,595,439 | 7/1971 | Newby | 206/63.5 |
| 3,664,508 | 2/1972 | Kobernick | 206/222 |
| 3,684,136 | 8/1972 | Baumann | 604/87 |
| 3,739,947 | 6/1973 | Baumann et al. | 222/136 |
| 3,762,540 | 10/1973 | Baumann et al. | 206/63.5 |
| 3,826,409 | 7/1974 | Chilcoate | 222/574 |
| 4,449,645 | 5/1984 | Korwin | 222/136 |
| 4,515,267 | 5/1985 | Welsh | 222/386 |
| 4,518,386 | 5/1985 | Tartaglia | 206/219 |
| 4,572,412 | 2/1986 | Brach et al. | 222/574 |
| 4,648,532 | 3/1987 | Green | 222/136 |
| 4,664,299 | 5/1987 | Goncalves | 222/80 |
| 4,793,475 | 12/1988 | Itzel | 206/221 |
| 4,852,772 | 8/1989 | Ennis, III | 222/386 |
| 4,893,734 | 1/1990 | Chlystun | 222/572 |
| 4,941,751 | 7/1990 | Muhlbauer | 206/63.5 |
| 4,963,093 | 10/1990 | Dragan | 433/90 |
| 4,969,816 | 11/1990 | Drumm | 433/90 |
| 5,005,732 | 4/1991 | Penn | 222/91 |
| 5,026,283 | 6/1991 | Osanai et al. | 206/63.5 |

Primary Examiner—David T. Fidei
Attorney, Agent, or Firm—Paul A. Fattibene; Arthur T. Fattibene

[57] ABSTRACT

A dental capsule for mixing a cement powder with an activating liquid having a frangible seal. The frangible seal is placed between a nozzle and the body portion of a capsule preventing unmixed cement from entering the nozzle. The nozzle has a circumferential groove facilitating positioning thereof. A vent formed in the body of the capsule prevents premature rupturing of the frangible seal upon insertion of the plug. A second and third embodiment use a two-part plug for dispensing activating liquid to the cement powder contained within the body of the capsule.

20 Claims, 3 Drawing Sheets

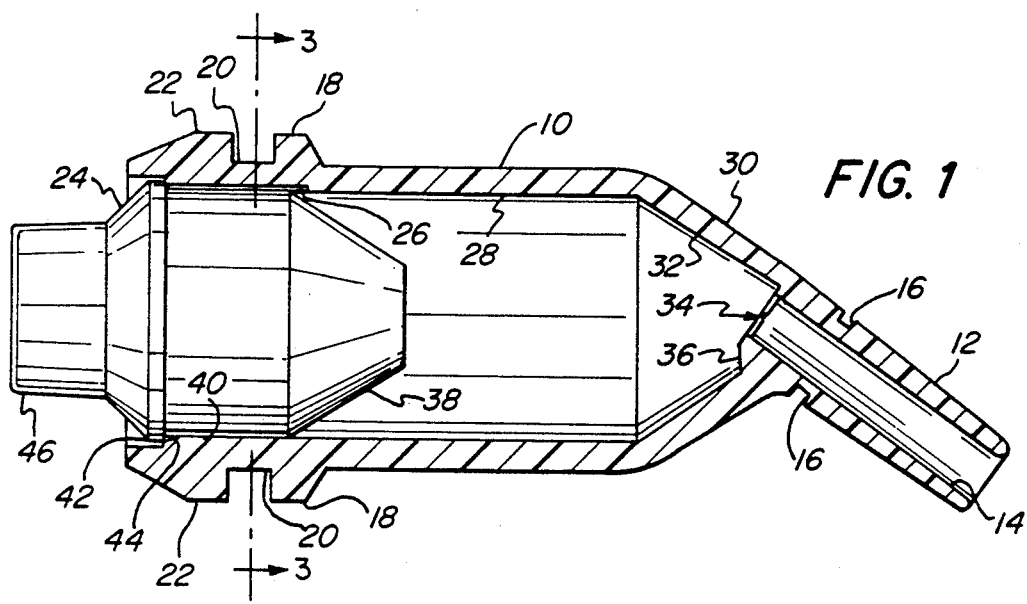
FIG. 1
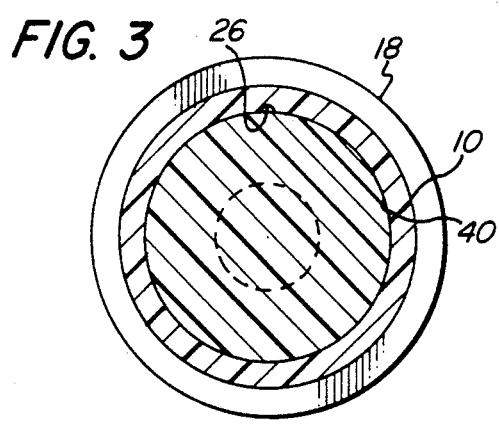
FIG. 3
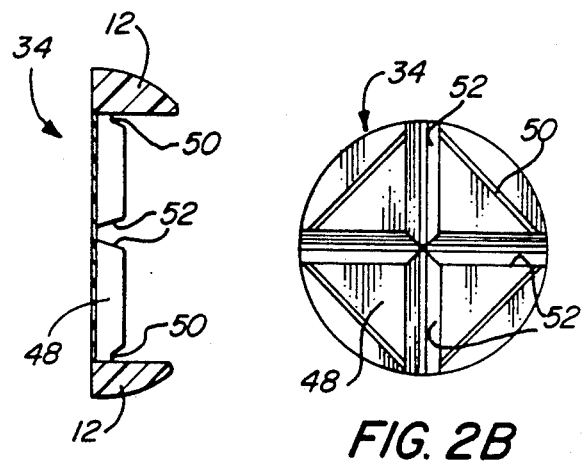
FIG. 2A
FIG. 2B
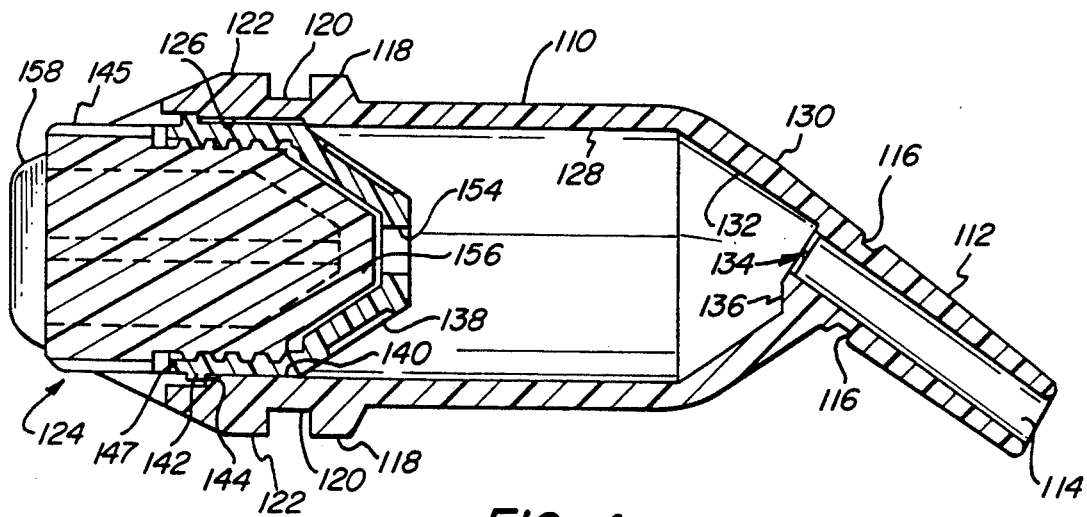
FIG. 4

CEMENT MIXING CAPSULE

FIELD OF THE INVENTION

The present invention relates generally to a capsule for mixing a liquid activated powder cement as used in dentistry, and particularly to an improved capsule making it easier for the dentist to mix and apply liquid activated cement powders.

BACKGROUND OF THE INVENTION

In dentistry, it is common to use various cements for different procedures. One such type of cement that is commonly used is a powder cement that is activated by a liquid forming a mixture that is applied in various dental procedures. Typically, the dentist must mix the cement powder and activating liquid on a slab or pallet by hand and apply the mixed cement to a prepared tooth with a spatula or other suitable hand instrument. The dentist can also place the mixed cement into an empty tube for application with an applicator gun or a syringe. The mixing and placement of these types of powder cements being activated with a liquid activator has proven to be messy and difficult. In efforts to solve these problems and to provide a more convenient method and apparatus to apply liquid activated powder cements, relatively complex capsules have been created requiring costly and specially designed apparatus to use them. Generally, a specially designed capsule is used containing a quantity of cement powder and a separate section containing the activating liquid. Either a specially designed folding nozzle or a separate pin inserted into the nozzle is used to prevent the cement powder from entering the nozzle prior to mixing. If the cement powder enters the nozzle prior to mixing, the powder contained therein will not mix properly, resulting in clogging or improperly applied cement. Special apparatus or devices are needed to crush the portion of the capsule containing the activating liquid. A shaker or amalgamator is then used to thoroughly mix or amalgamate the cement powder with the activating liquid to result in a homogeneous mixture of cement. The capsule is then removed from the amalgamator and placed within a gun or applicator for dispensing the cement. These complicated devices, while attempting to make the application of a cement powder activated by a liquid more convenient for the dentist, have resulted in more complex, costly and difficult procedures for the dentist. Therefore, there is a need for a simpler, less complex capsule and system for applying liquid activated cement powder that can be more easily and conveniently used by a dentist, resulting in less cost.

SUMMARY OF THE INVENTION

The present invention comprises a simple and convenient cement mixing capsule. The capsule comprises a body with a nozzle attached to one end. A plug is inserted in the other end of the body and acts as a piston. A vent is provided along a longitudinal portion of the body to facilitate insertion of the plug. A frangible seal is placed between the body and the nozzle, preventing cement powder from entering the nozzle prior to mixing. A circumferential groove is placed around the nozzle to permit positioning of the nozzle and assist placement of the cement. In a second embodiment, a two-part plug comprising an internally threaded plug and a threaded plug insert is used to administer the activating liquid to the cement powder contained within the body portion of the capsule. When the threaded plug insert is advanced, a packet of activating liquid is compressed causing it to burst and dispense the activating liquid into the body containing the cement powder. This is done easily by hand. The cement is then mixed prior to dispensing. In a third embodiment, a two-part plug comprising a cylinder and a piston and a second frangible diaphragm is used to dispense the activating liquid placed directly within the cylinder in the plug.

Accordingly, it is an object of the present invention to provide a simple and easy to use capsule for mixing and dispensing dental cement of the type consisting of a cement powder and activating liquid.

It is an advantage of the present invention that it can be operated by hand requiring no special equipment to combine the activating liquid with the cement powder.

It is another advantage of the present invention that the nozzle can be sealed preventing powder from clogging the nozzle before mixing.

It is a feature of the present invention that a frangible seal is placed between the body and nozzle of the capsule.

It is another feature of the present invention that a longitudinal vent is provided at the open end of the capsule to facilitate placement of the plug and prevent premature rupture of the frangible seal.

It is yet another feature of the present invention that a circumferential groove is inscribed around the nozzle so that the nozzle can be placed at different angular positions.

These and other objects, advantages, and features will become more readily apparent in view of the following detailed description.

BRIEF DESCRIPTION OF THE DRAWINGS

FIG. 1 is a cross section of a first embodiment of the present invention.

FIG. 2A is a cross section more clearly illustrating the frangible seal of the present invention.

FIG. 2B is a plan view more clearly illustrating the frangible seal of the present invention.

FIG. 3 is a cross section taken along line 3—3 in FIG. 1.

FIG. 4 is a cross section of a second embodiment of the present invention.

DETAILED DESCRIPTION OF THE PREFERRED EMBODIMENTS

Figure 5:
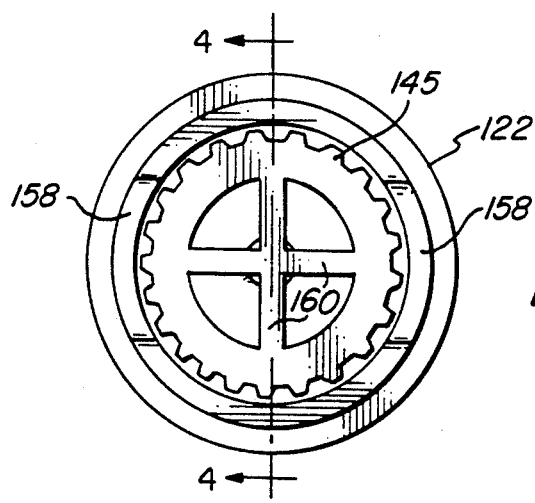
FIG. 5 is an end view of the present invention.

FIG. 1 illustrates the first embodiment of the present invention. A body 10 has an angularly disposed nozzle 12 thereon. The nozzle 12 has a bore 14 therein. Nozzle 12 has a circumferential groove 16 therein. The circumferential groove 16 permits the nozzle 12 to be bent to any preferred angular position facilitating placement of the dental cement contained within the body 10. At the rear of body 10 is an annular front collar 18, an annular rear collar 22, and an annular channel disposed therebetween. The front collar 18, channel 20, and rear collar 22 act as a means for securely holding the body 10 of the capsule within an extrusion device or handle, not shown. Plug 24 is positioned in the open end of body 10 near the rear collar 22. A vent 26 extends a longitudinal distance within bore 28 of body 10. The vent 26 extends a longitudinal distance slightly longer than the sealing surface 40 of plug 24. Plug 24 has a handle or grip 46 permitting easy grasping of the plug 24. Plug 24 also has a front end 38. The front end 38 is of a size to complement the interior surface 32 of the front end 30 of body 10. The front end 30 of body 10 also incorporates a plug stop 36. Adjacent the interior opening of bore 14 and the discharge end of interior bore 28 is a frangible seal 34. The frangible seal 34 seals the inlet of nozzle bore 14. This prevents nozzle bore 14 from being clogged as well as preventing contamination from entering the bore 28 of the body 10. The frangible seal 34 is constructed so as to easily rupture or break.

The end opposite the nozzle 12 of body 10 has a shoulder 44. A positioning ring 42 is attached to the plug 24. The diameter of the positioning ring 42 is slightly greater than that of the diameter of sealing surface 40. Thereby, when plug 24 is placed within bore 28 of the body 10, the plug 24 only advances until the positioning ring 42 strikes the shoulder 44 on body 10. This prevents the plug 24 from unintentionally advancing forward within the bore 28. The positioning ring 42 can be made of a malleable or frangible material such that when a predetermined amount of force is applied, the positioning ring 42 will bend or break away, resulting in the advancement of plug 24 toward the nozzle 12.

FIGS. 2A and 2B more clearly illustrate the frangible seal 34. The frangible seal 34 is comprised of a flap 48 attached by a circumferential hinge 50 to the nozzle 12. Notches 52 extend deep within flap 48 resulting in a very thin material at the bottom thereof. As a result, the flap 48 is easily separated into multiple flaps that fold withon hinge 50, permitting material to flow therethrough.

FIG. 3 more clearly illustrates the longitudinal vent 26 formed within the body 10 along the bore 28. The vent 26 permits displacement of air when inserting plug 24 within bore 28 of body 10. This results in much easier insertion of plug 24, while also preventing the premature rupturing of frangible seal 34 due to the possible increase of pressure during insertion of plug 24.

The operation of the present invention can be readily appreciated with reference to FIGS. 1-3. The capsule of the present invention is provided empty or pre-dosed with a quantity of cement powder contained therein. Once the cement powder is placed within the body 10 of the capsule, it is prevented from entering nozzle bore 14 by frangible seal 34. If the capsule has a pre-dosed or predetermined amount of cement powder contained therein, the dentist need only remove the plug 24 by grasping handle or grip 46 to place a quantity of activating liquid therein. The dentist can accurately dispense a quantity of activating liquid in order to obtain the desired consistency, set time, or other qualities of the mixed cement desired by the dentist. The individual application by the dentist of activating liquid has the advantage, in that the dentist can tailor the cement mix to a preferred consistency. This is not possible in applications where a predetermined volume of activating liquid comes prepackaged with the capsule. After placement of the predetermined quantity of activating liquid within the bore 28 of the capsule, the dentist merely replaces the removable plug 24 abutting the positioning ring 42 adjacent the shoulder 44. The capsule is then mixed as conventionally done on a shaker or amalgamator to thoroughly mix the cement powder and activating liquid. During this process, the frangible seal 34 prevents any entering of an incomplete mixture within the nozzle bore 14. Once amalgamation has taken place, the dentist merely removes the capsule from the amalgamator or shaker and inserts the capsule into a conventional applicator or gun which holds the body 10 by the channel 20 therein. The dentist can position the nozzle 12 with the aid of circumferential groove 16 into any desired angular position to assist placement of the mixed cement within a tooth or other oral cavity. Upon extrusion, the positioning ring 42 on the plug 24 will break or deform permitting the plug 24 to advance within bore 28. As pressure builds up within bore 28 due to the advancing plug 24, the frangible seal 34 will be forced to rupture, resulting in thoroughly mixed cement being extruded from nozzle 12 through bore 14. It should be appreciated that vent 26 permits the placement of plug 24 within bore 28 until the positioning ring 42 abuts shoulder 44 without any appreciable increase in pressure within bore 28, thereby preventing the premature rupture of frangible seal 34. However, when material is to be extruded and the plug 24 is advanced, and the sealing surface 40 extends beyond the furthest forward longitudinal extent of vent 26, thereby sealing bore 28, pressure will build up therein causing the rupturing of frangible seal 34 and the extrusion of cement through nozzle 12. Thereby, the dentist has a very convenient means for dispensing cements that must be mixed from a powder and liquid activator.

FIG. 4 illustrates a second embodiment of the present invention. The capsule illustrated therein is similar to that illustrated in FIG. 1, with the exception of plug assembly 124 and support fingers 158. Body 110 has a nozzle 112 connected thereto. Nozzle 112 has a bore 114 therein. Nozzle 112 has a circumferential groove 116. At the opposite end of body 110 is a front collar 118, rear collar 122, and a channel 120 therebetween. The plug assembly 124 fits within bore 128 of body 110. A vent 126 is formed longitudinally within bore 128. The interior surface 132 of the front 130 of body 110 has a complimentary shape to that of the front of plug assembly 124. A plug stop 136 is formed within the front 130. A frangible seal 134, identical to that as illustrated in FIGS. 2A-2B, seals the bore 114 of nozzle 112.

The plug assembly 124 is comprised of an internally threaded plug 147 and a threaded plug insert 145. The internally threaded plug 147 has a front end 138 and a sealing surface 140. Additionally, a positioning ring 142 is formed thereon. Positioning ring 142 is frangible or malleable. A shoulder 44 is formed on body 110 to mate with the positioning ring 142. The internally threaded plug 147 has an opening 154 therein which communicates With the interior of bore 128. The threaded plug insert 145 has a front end 156 that when fully seated abuts the opening 154.

FIG. 5 illustrates the rear of the capsule of the present invention. The support fingers 158 can more clearly be seen as can the threaded plug insert 145. Threaded plug insert 145 is made with support ribs 160 to provide rigidity and save material. The outer diameter of threaded plug insert 145 has ridges thereon so as to facilitate easier grasping and turning.

Figure 6:
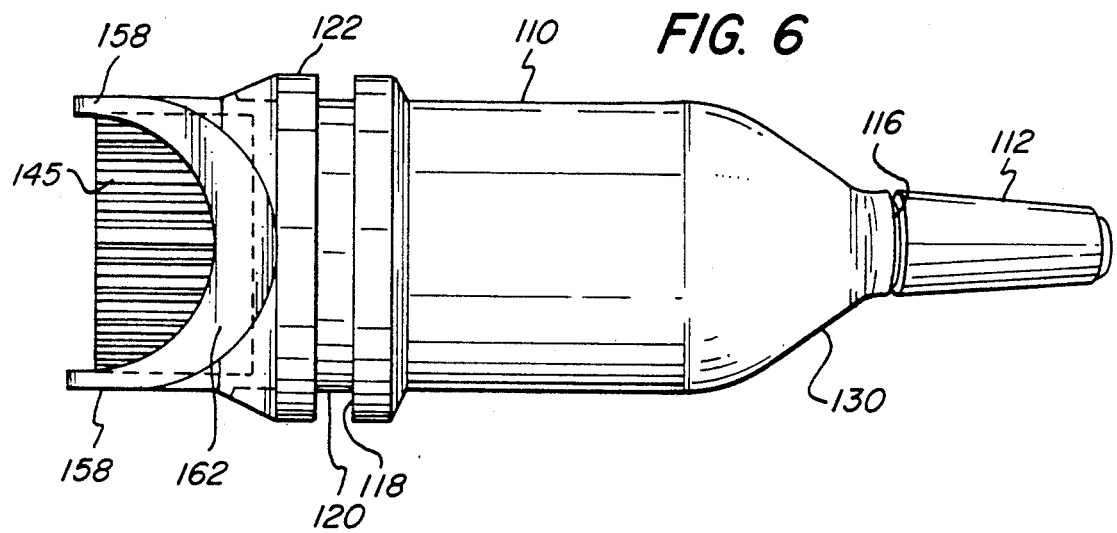
FIG. 6 is a top plan view of the present invention.
Figure 7:
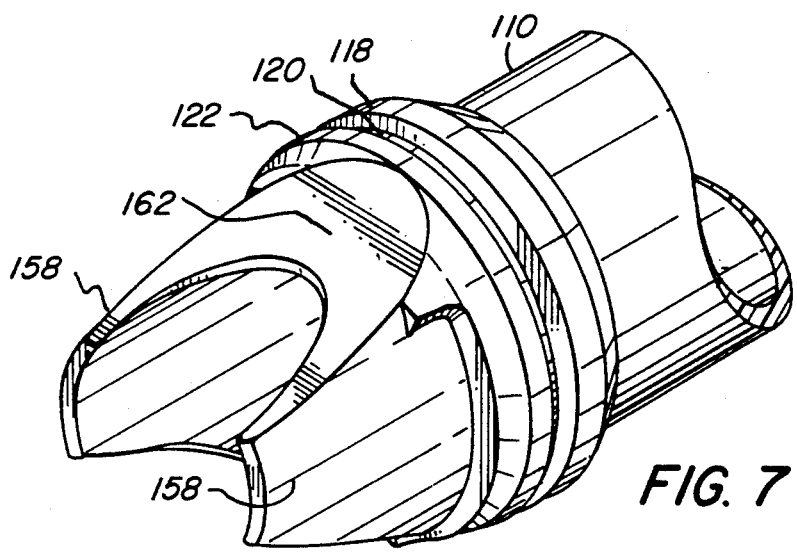
FIG. 7 is a perspective view more clearly illustrating the support fingers of the present invention.

FIG. 6 and FIG. 7 more clearly illustrate the support fingers 158. The support fingers 158 provide protection for the plug assembly 124, but yet permit the threaded plug insert 145 to be rotated. This is accomplished by the support fingers 158 being cut away at the top and bottom, and the beveled surfaces 162 thereon. Additionally, the support fingers 158 provide a means for securely placing the capsule within a standard shaker or amalgamator without effecting or contacting the plug assembly 124.

The functioning of the present invention can easily be appreciated with reference to FIGS. 4-7. The capsule of this, the second embodiment, as illustrated in FIGS. 4-7, is used to prepackage a predetermined quantity of cement powder together with a predetermined quantity of activating liquid. The cement powder is placed directly within the bore 128 of the body 110. The cement powder is prevented from entering nozzle bore 114 by frangible seal 134. A packet, not shown, of activating liquid is placed within plug assembly 124 between the internally threaded plug 147 and the threaded plug insert 145 adjacent the opening 154. The plug assembly 124 is then positioned within the bore 128 of body 110. The capsule and cement therein can easily be prepared without the need of any specialized apparatus by simply rotating threaded plug insert 145 such that the end 156 is advanced forward crushing the packet, not shown, containing activating liquid. Upon rupturing, the activating liquid is dispensed within the bore 128. The capsule can then be shaken with a standard amalgamator to thoroughly mix the cement powder and activating liquid, and dispensed as previously described with respect to FIGS. 1-3. Should the internally threaded plug 147 rotate upon the turning of threaded plug insert 145, the internally threaded plug 147 can be keyed to the bore 128 preventing rotation thereof.

Figure 8:
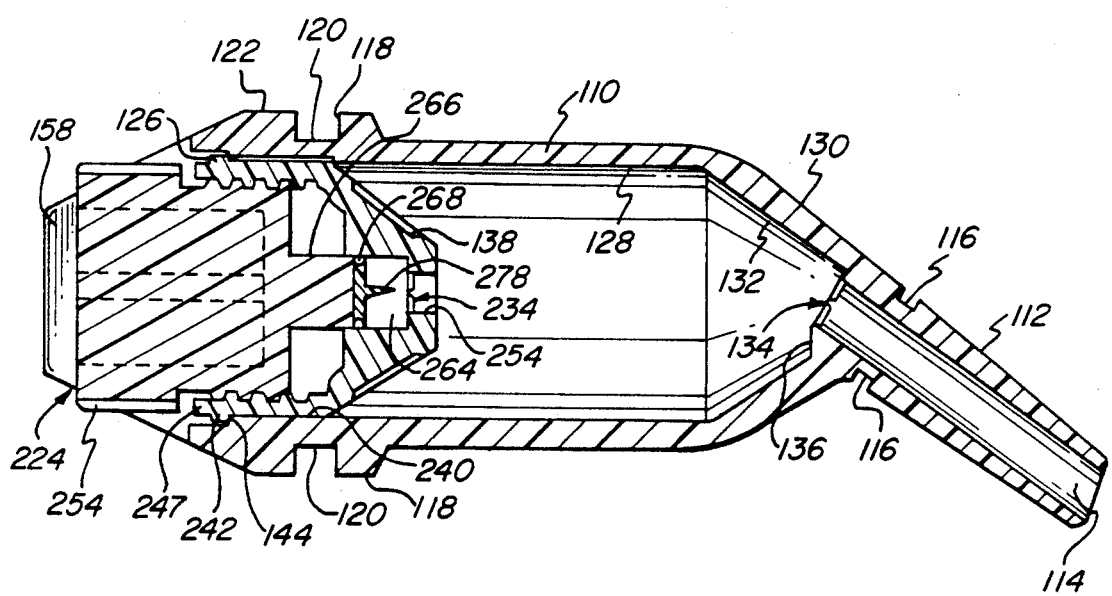
FIG. 8 is a cross section of a third embodiment of the present invention.

FIG. 8 illustrates a third embodiment illustrating a second plug assembly 224. The plug assembly 224 comprises an internally threaded plug 247 having a cylinder 264 therein adjacent an opening 254. A second frangible seal 234 is positioned between the cylinder 264 and the opening 254. Internally threaded plug 147 has an exterior sealing surface 240 that seals the plug assembly 224 within bore 128. The sealing surface 240 extends just short of the end of longitudinal vent 126, thereby permitting easy insertion of the plug assembly 224 within bore 128 without prematurely rupturing frangible seal 134 adjacent the nozzle bore 114. Threaded within the internally threaded plug 247 is a threaded plug insert 245. Threaded plug insert 245 has a piston 266 on the end thereof. Piston 266 is adapted to fit within cylinder 264. A seal 268 aids in sealing the interior of cylinder 264. On the end of piston 266 is a lance 270. Lance 270 is used to pierce the second frangible seal 234. However, in most applications lance 270 will not be needed. The advancing piston 266 will generally provide sufficient pressure to rupture frangible seal 234.

This, the third embodiment, as illustrated in FIG. 8 avoids the use of a sealed packet containing activating liquid as used in the second embodiment illustrated in FIG. 4. Activating liquid can be placed directly within the cylinder 264. The second frangible seal 234 prevents the activating liquid from entering the bore 128 and contacting the cement powder contained therein. When the capsule is to be used, the dentist merely rotates the threaded plug insert 145 advancing the piston 266 into cylinder 264 causing the second frangible seal 234 to rupture, thereby dispensing the activating liquid. The activating liquid and cement powder can then be mixed as previously described. The plug assembly 224 can then be advanced as previously described to rupture frangible seal 134, resulting in dispensing of the mixed cement.

In most applications the dentist will likely wish to rely on the pressure within the bore 28 or 128 due to the advancing plug or plug assembly 124 or 128 to rupture the frangible seal 34 or 134. However, in some applications, or when the dentist desires greater control the frangible seal 34 or 134 can be ruptured by inserting a long pin or wire into the nozzle bore 114 after mixing an prior to dispensing.

The present invention as described, therefore, provides a simple, cost effective solution to the dentist desiring to use cement powders with liquid activators that is easy to use and avoids the cost, complex structure, and specialized equipment previously required in order to administer liquid activated cement powders.

Although the preferred embodiments have been illustrated and described, it will be obvious to those skilled in the art that various modifications may be made without departing from the spirit and scope of this invention.

What is claimed:

1. A dental cement mixing capsule comprising:
   a tubular body having a first bore, a front end, and a back end;
   collar means, attached adjacent to the back end of said body, for securely holding said body;
   a nozzle having a second bore therein attached to the front end of said body;
   a frangible seal integrally molded between said first bore and said second bore, said frangible seal breaking solely as a result of pressure developed within the first bore;
   a plug adapted to initially fit partially within the bore, said plug having an inserting end, sealing surface, and an extending end;
   positioning ring means, attached to the extending end of said plug, for preventing said plug from unintentionally advancing into the first bore;
   said tubular body having a longitudinally extending vent with an axial length slightly greater than the distance between said positioning ring means and the furthermost portion of the sealing surface; and
   handle means, placed on the extending end of said plug, for facilitating removing and replacing said plug.

2. A dental cement mixing capsule as in claim 1 wherein:
   said frangible seal comprises a flap having a circumferential hinge and at least one notch extending between said circumferential hinge.

3. A dental cement mixing capsule as in claim 1 wherein:
   said positioning ring means is malleable.

4. A dental cement mixing capsule as in claim 1 wherein:
   said positioning ring means is frangible.

5. A dental cement mixing capsule as in claim 1 wherein:
   said nozzle is angularly disposed to the longitudinal axis of said body.

6. A dental cement mixing capsule as in claim 1 wherein:
   said nozzle has a circumferential groove therein.

7. A dental cement mixing capsule as in claim 1 wherein:
   said collar means comprises a front collar, a rear collar, and a channel disposed therebetween.

8. A dental cement mixing capsule as in claim 6 wherein said first bore is cylindrical.

9. A dental cement mixing capsule comprising:

a tubular body having a first bore, a front end, and a back end;

collar means, attached adjacent to the back end of said body, for securely holding said body;

a nozzle having a second bore therein attached to the front end of said body;

a frangible seal disposed between said first bore and said second bore;

an internally threaded plug having an opening in the front thereof and adapted to be received by said first bore; and a threaded plug insert mating with said internally threaded plug.

10. A dental cement mixing capsule as in claim 9 wherein:

said frangible seal comprises a flap having a circumferential hinge and at least one notch extending between said circumferential hinge.

11. A dental cement mixing capsule as in claim 10 wherein:

said nozzle has a circumferential groove therein.

12. A dental cement mixing capsule as in claim 11 further comprising:

support fingers placed adjacent the back end of said tubular body and extending longitudinally beyond said threaded plug insert.

13. A dental cement mixing capsule as in claim 12 wherein:

said tubular body has a vent disposed from the back end thereof.

14. A dental cement mixing capsule comprising:

a tubular body having a first bore, a front end, and a back end;

collar means, attached adjacent to the back end of said body, for securely holding said body;

a nozzle having a second bore therein attached to the front end of said body;

a first frangible seal disposed between said first bore and said second bore;

an internally threaded plug having an open back end and a front end having a cylinder formed therein with an opening;

a threaded plug insert mating with said internally threaded plug;

a piston attached to said threaded plug insert adapted to fit within the cylinder; and a second frangible seal placed within the opening between the cylinder and the first bore.

15. A dental cement mixing capsule as in claim 14 further comprising:

a lance positioned on said piston.

16. A dental cement mixing capsule as in claim 15 wherein:

said nozzle has a circumferential groove therein.

17. A dental cement mixing capsule as in claim 14 further comprising:

support fingers attached to the back end of said tubular body and extending longitudinally beyond said threaded plug insert.

18. A dental cement mixing capsule comprising:

a tubular body having a first bore, a front end, and an open back end;

a back collar attached adjacent to the open back end of said tubular body;

a front collar attached forward and adjacent to said back collar having a channel disposed between said back collar and said front collar;

an angularly disposed nozzle having a second bore therein attached to the front end of said tubular body and having a circumferential groove formed in the exterior surface thereof near the end of said nozzle attached to the front end of said tubular body;

a frangible seal disposed between said first bore and said second bore and having a circumferential hinge around the exterior thereof and a first notch and a second notch orthogonal to the first notch, said first and second notches extending between the edges of the circumferential hinge and having a depth slightly less than the axial thickness of said frangible seal;

an internally threaded plug having an opening in the front thereof and adapted to be received by said first bore, said internally threaded plug having a sealing surface thereon which contacts the first bore;

a malleable positioning ring formed on the exterior circumference of the back end of said internally threaded plug;

a shoulder mating with said malleable positioning ring formed within said tubular body adjacent the open back end;

a vent groove formed in said tubular body adjacent the open back end on the interior surface of the first bore and extending a longitudinal length slightly greater than the length of the sealing surface on said internally threaded plug;

a threaded plug insert mating with said internally threaded plug having a front portion that complements the interior front portion of said internally threaded plug; and a pair of support fingers extending from the open back end of said tubular body slightly beyond the end of said threaded plug insert.

19. A dental cement mixing capsule comprising:

a tubular body having a first bore, a front end, and a back end;

collar means, attached adjacent to the back end of said body, for securely holding said body;

a nozzle having a second bore therein attached to the front end of said body;

a frangible seal integrally molded between said first bore and said second bore, said frangible seal breaking solely as a result of pressure developed within the first bore;

an internally threaded plug having an opening in the front thereof and adapted to be received by said first bore, said internally threaded plug having an inserting end, sealing surface, and extending end;

positioning ring means, attached to the extended end of said internally threaded plug, for preventing said internally threaded plug from unintentionally advancing into the first bore;

said tubular body having a longitudinally extending vent with an axial length slightly greater than the distance between said positioning ring means and the furthermost portion of the sealing surface; and a threaded plug insert mating with said internally threaded plug.

20. A dental cement mixing capsule as in claim 14 wherein: the cylinder has a cross sectional area substantially less than the cross sectional area of the first bore, whereby small quantities of liquid can be accurately dispensed.

* * * * *